United States Patent [19]

Faust et al.

[11] Patent Number: 5,169,759
[45] Date of Patent: Dec. 8, 1992

[54] REMOVAL OF RIBOFLAVIN FROM FERMENTATION SUSPENSIONS

[75] Inventors: Tillmann Faust, Weisenheim; Joachim Meyer, Hessheim; Georg Wellinghoff, Mannheim; Walter Gösele, Heidelberg; Christoph Martin, Mannheim; Johannes Grimmer, Ludwigshafen, all of Fed. Rep. of Germany

[73] Assignee: BASF Aktiengesellschaft, Ludwigshafen, Fed. Rep. of Germany

[21] Appl. No.: 644,609

[22] Filed: Jan. 23, 1991

[30] Foreign Application Priority Data

Jan. 25, 1990 [DE] Fed. Rep. of Germany ....... 4002066

[51] Int. Cl.⁵ .............. C12P 25/00; C12P 19/38; C12P 7/58
[52] U.S. Cl. .......................... 435/66; 435/87; 435/101; 435/105; 435/137
[58] Field of Search ............ 435/66, 87, 101, 105, 435/137

[56] References Cited

U.S. PATENT DOCUMENTS

| | | | |
|---|---|---|---|
| 3,494,542 | 2/1970 | Craig et al. | 233/7 |
| 4,165,250 | 8/1979 | Epstein et al. | 435/267 |
| 4,355,158 | 10/1982 | Wolf et al. | 435/137 |
| 4,794,081 | 12/1988 | Kawai et al. | 435/66 |
| 4,840,899 | 6/1989 | Pochodylo | 435/87 |
| 4,946,780 | 8/1990 | Hashimoto et al. | 435/101 |
| 4,957,475 | 9/1990 | Krell et al. | 494/53 |
| 4,966,845 | 10/1990 | Stack | 435/105 |

FOREIGN PATENT DOCUMENTS

| | | | |
|---|---|---|---|
| 211289 | 7/1986 | European Pat. Off. | |
| 231605 | 11/1986 | European Pat. Off. | |
| 0338596 | 10/1989 | European Pat. Off. | 435/66 |
| 0341433 | 11/1989 | European Pat. Off. | 435/66 |
| 1920592 | 12/1969 | Fed. Rep. of Germany | |
| 1925001 | 12/1969 | Fed. Rep. of Germany | 435/66 |

OTHER PUBLICATIONS

Winnacker, Küchler, Chem. Technologie, 1984, Band 1, p. 73ff.
Ulmanns Encyklopädie der technischen Chemie, 4., Auflage, Band 2 pp. 204-213, especially 208-210.

Primary Examiner—David M. Naff
Assistant Examiner—L. Blaine Lankford
Attorney, Agent, or Firm—Keil & Weinkauf

[57] ABSTRACT

Riboflavin is removed from fermentation suspensions by them being heated at from 50° to 90° C. for from 1 to 3 hours, than cooled to from 0° to 30° C. over a period of from 1 to 5 hours, and subsequently being centrifuged to give a sediment fraction and liquid fraction in such a way that the sediment fraction contains predominantly riboflavin crystals as solid, and the liquid fraction contains virtually no crystalline riboflavin, and, where appropriate, resuspending the sediment fraction in from 0.5 to 2 parts by volume of water per part by volume of sediment fraction and repeating procedure c.

8 Claims, 1 Drawing Sheet

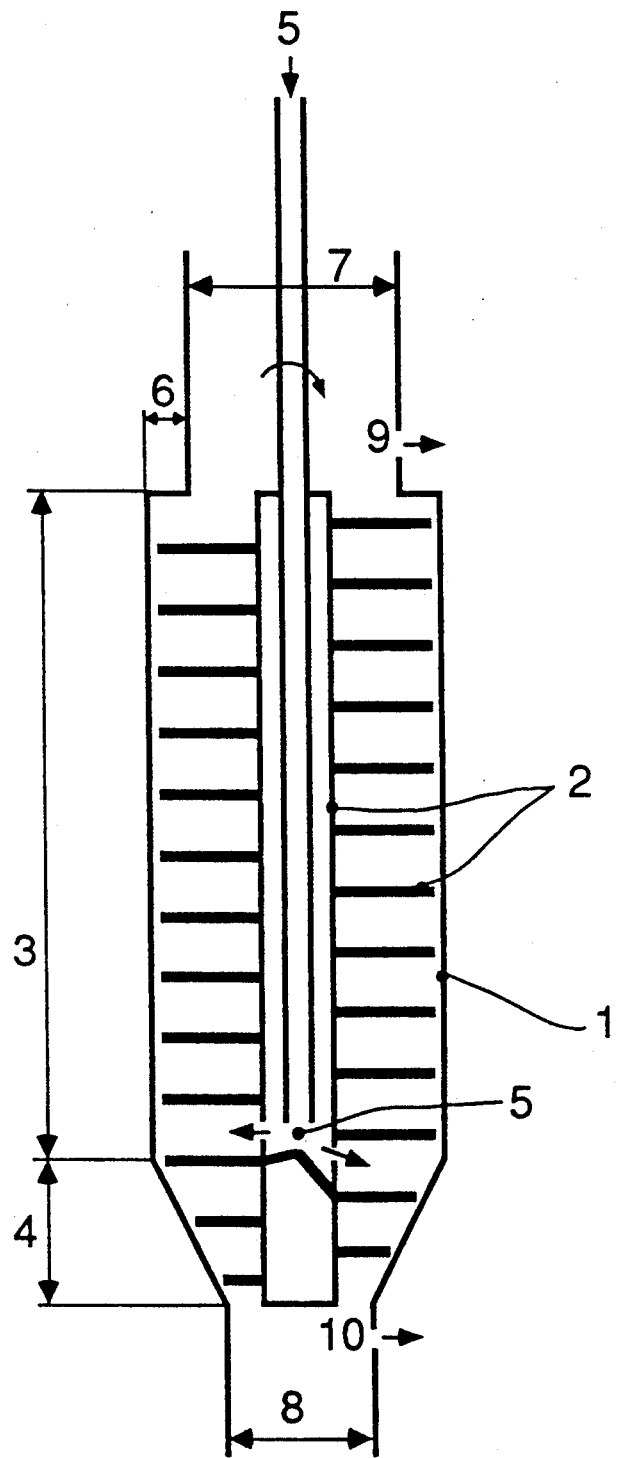

REMOVAL OF RIBOFLAVIN FROM FERMENTATION SUSPENSIONS

The present invention relates to an improved process for removing riboflavin from fermentation suspensions by centrifugation.

DE-C 2 920 592 discloses a process for removing riboflavin from fermenter suspensions in which the fermentation suspensions are diluted with from 25 to 100% by volume of water and subsequently heated at from 50° to 65° C. for from 15 to 45 minutes. After the suspensions have been cooled they are centrifuged twice to concentrate the riboflavin. The consequence of the dilution is that a larger volume of fermenter suspension has to be processed, which increases the costs of processing and the losses of riboflavin owing to some dissolving in the added water.

It is an object of the present invention to remove riboflavin from fermenter suspensions with minimal loss of riboflavin to give a solid with a maximum riboflavin content.

We have found that this object is achieved by a process for removing riboflavin from fermentation suspensions by centrifugation, which comprises a) the fermentation suspensions being heated at from 50° to 90° C. for from 1 to 3 hours and then
b) being cooled to from 0° to 30° C. over a period of from 1 to 10 hours, and subsequently
c) being centrifuged to give a sediment fraction and a liquid fraction in such a way that the sediment fraction contains mainly riboflavin crystals as solid, and the liquid fraction contains virtually no crystalline riboflavin,
d) if desired resuspending the sediment fraction with from 0.5 to 2 parts by volume of water per part by volume of sediment fraction, and repeating procedure (c) one or more times.

The riboflavin fermentation suspensions can be obtained by conventional processes (see, for example, EP-A 231 605, EP-A 211 289; T. Szczesniak et al., Acta Microbiologica Polonica Ser. B, 3 (1971) 29-34 and 91-95), for example using mutants of yeast cells of the genus Saccharomyces, mutants of the strains *Candida flareri* GA 18Y8-6#2 and 6A 18Y8-6#2#11 and mutants of the strain *Ashbya gossypii*.

These fermentation suspensions contain up to 20% by weight of riboflavin based on the total solids content of the suspensions. The remaining solids are essentially composed of complex cellular constituents.

It is essential for the process according to the invention that the fermenter suspension is heated, preferably for from 1 to 3 hours, in particular for from 1 to 2 hours. This brings about a transformation in the riboflavin crystals in which predominantly larger crystals are formed at the expense of smaller ones.

The transformation is preferably carried out at from 55° to 80° C., in particular from 60° to 75° C.

The fermentation suspension is cooled to from 0° to 30° C. preferably over a period of from 1 to 8 hours, in particular 1 to 5 hours. This achieves a further optimization in the form of the riboflavin crystals.

The characteristics of the riboflavin crystals produced in this way make it possible, when suitable equipment is used, to separate the crystals optimally from the complex constituents of the cells and the media, which have lower specific gravities, in the fermentation suspensions, i.e. to fractionate into a sediment fraction predominantly containing riboflavin crystals as solid and into a liquid fraction which contains virtually no crystalline riboflavin but does contain a large part of the complex cellular constituents.

Suitable equipment for removing riboflavin from the fermenter suspensions comprises decanter-type centrifuges which allow separation into two fractions when operated on the classification principle. Classification means the separation of a slurry only into a more or less dewatered cake and an overflow containing the fine sediments (cf. Winnacker, Richter, Chemische Technologie, 1984, volume 1, pages 73 et seq.).

A particularly advantageous design of the process to be used for the centrifugation of the heat-treated fermenter suspension is a decanter-type centrifuge with full casing and a helical conveyor, as depicted in the FIGURE, where the numbers (1) to (10) have the following meanings:

(1) bowl
(2) helical conveyor
(3) cylindrical sedimentation part
(4) conical dewatering part
(5) suspension feed
(6) adjustable overflow height
(7) overflow diameter
(8) sediment discharge diameter
(9) liquid drain
(10) sediment discharge.

The geometry and the operation are optimized for the suspension of riboflavin crystals recrystallized according to the invention. The important parameters are the shape and speed of rotation of the bowl, the differential speed of rotation of the helical conveyor, the overflow height (6) and the suspension throughput, i.e. the surface loading.

In order to compensate for variations in the riboflavin suspension with regard to solids content and the ratio of riboflavin to biomass and other constituents of the media in the suspension, the centrifuge ought to have the largest possible active classification area. This is achieved, on the one hand, by using a bowl (1) with a high slenderness ratio (slenderness ratio = length/diameter of the centrifuge), i.e. a slenderness ratio of from 3 to 6, preferably of 4 or above, and, on the other hand, by shifting the ratio of the cylindrical sedimentation part (3) to the conical dewatering part (4) in favor of the sedimentation part by designing the conical part with an angle of, advantageously, from 10° to 25°, especially from 10° to 17°.

The suspension feed (5) is preferably sited approximately at the junction between the cylindrical and the conical parts of the centrifuge.

The overflow height (6) of the decanter must also be suited to the riboflavin crystal suspension. This preferably entails using an overflow diameter (7) which is about ±10 mm different from the sediment discharge diameter (8). If the selected height (6) is too great (when the overflow diameter < sediment discharge diameter), there may be a short circuit leading to emergence of feed suspension at the sediment discharge, which reduces product purity. If the height is too low (when the overflow diameter > sediment discharge diameter), piling up of solid in the dewatering part leads to increased losses in riboflavin in the overflow.

In order to achieve an optimal classification between the riboflavin crystals on the one hand and the cell material and the constituents of the media on the other hand, i.e. to have an optimal residence time in the decanter, it is necessary to match the speed of rotation of the bowl, the differential speed of rotation of the helical conveyor and the suspension throughput for a given decanter size. For example, if the selected speed of rotation of the bowl is too low at a given suspension throughput, the insufficient centrifugal force results in an increased loss of riboflavin crystals in the overflow. On the other hand, if the selected speed of rotation is too high, the increased sedimentation of cell material and constituents of the media results in a smaller improvement in product purity.

Hence the present invention also relates to a process, as defined above, for removing riboflavin from fermentation suspensions, which comprises the fermentation suspension being centrifuged in step c) to give a sediment fraction and a liquid fraction so that at least 60% of the solids in the sediment fraction is composed of riboflavin crystals, and the liquid fraction still contains a large part of the complex cellular constituents. This can advantageously be achieved by carrying out the centrifugation in step c) in a decanting centrifuge operated by the classification principle. It is particularly advantageous for the centrifugation in step c) to be carried out in a decanter-type centrifuge with full casing and a helical conveyor and with a slenderness ratio of 4 or greater and a conical part with an angle of from 10° to 25°, and operating it on the classification principle, with the overflow diameter being equal to the sediment discharge diameter ±10 mm.

It is particularly advantageous for the differential speed of rotation of the helical conveyor to be from ±0.1% to ±1% of the speed of rotation of the bowl, and for the surface loading (= ratio of the suspension throughput to the equivalent settling area) to be from 0.8 to 1.8 $l/(m^2 \cdot h)$, preferably from 1 to 1.5 $l/(m^2 \cdot h)$, in the first decantation, and from 0.2 to 0.8 $l/(m^2 \cdot h)$, preferably from 0.4 to 0.6 $l/(m^2 \cdot h)$, if the decantation is repeated.

The centrifugation conditions are usually selected so that the resulting sediment fraction still contains from 65 to 90% by weight, preferably 70 to 85% by weight, of water.

The solid in the sediment fraction is more than 60% by weight riboflavin. It is possible to resuspend and recentrifuge the sediment fraction to increase the proportion of riboflavin in the total solids content further.

The sediment fractions are preferably resuspended in from 0.5 to 2 parts by volume, in particular 0.7 to 1.5 parts by volume, of water per part in volume of sediment.

The sediment fractions containing more than 60% by weight of riboflavin can be employed directly after the dewatering as animal feed additives or, after further purification, for pharmaceutical purposes.

The sediment fraction can be dried, for example, by fluidized bed spray granulation.

The process according to the invention can be used to obtain in a straightforward manner and with low riboflavin losses from fermentation suspensions up to about 60% pure riboflavin with a single decantation and about 75 to 88% pure riboflavin with repetition of the decanting procedure.

EXAMPLE 1

A fermentation suspension which was composed of about 85% by weight water and 15% by weight solid which contained about 17% by weight riboflavin was heated at 60° C. for two hours (h). The fermentation suspension was then cooled to 20° C. over the course of 5 hours. The suspension treated in this way was centrifuged in a centrifuge with full casing and a helical conveyor and with a slenderness ratio of 4, a conical part with an angle of 17°, an overflow diameter of 3 mm less than the sediment discharge diameter, a suspension feed approximately at the junction of the cylindrical and conical parts of the centrifuge and a surface loading of 1.3 $l/(m^2 \cdot h)$ in such a way that the sediment fraction was composed of 20% by weight solid and 80% by weight water.

The solid in the sediment fraction contained 63% by weight riboflavin, and the riboflavin losses were 1.8% by weight.

EXAMPLE 2

A fermentation suspension of the composition described in Example 1 was heated at 75° C. for one hour. Centrifugation was then carried out as in Example 1.

The resulting sediment fraction was composed of 66% by weight riboflavin, and the riboflavin losses were 1.9% by weight.

EXAMPLE 3

The sediment fraction obtained as in Example 1 was diluted with 0.8 part by volume of water per part by volume of sediment fraction and, for further concentration, centrifuged in a centrifuge with full casing and a helical conveyor and with a slenderness ratio of about 4, a conical part with an angle of 17°, equal overflow and sediment discharge diameters, a suspension feed approximately at the junction of the cylindrical sedimentation part with the conical dewatering part and with a surface loading of 0.5 $l/(m^2 \cdot h)$. The differential speed of rotation was adjusted to the rate of feed so that piling up of solid was thus prevented. The solid in the resulting sediment fraction contained 88% by weight riboflavin with the riboflavin losses being 1.0% of the crystal suspension employed in Example 1.

EXAMPLE 4

Comparative Example: Thermal Treatment And Centrifugation Not According To The Invention As in Example 1 of DE No. 29 20 592, a fermentation suspension of the composition described in Example 1 was heated to 60° C. over the course of 30 minutes (min), kept at 60° C. for 10 min and cooled to 20° C. over the course of 1 h.

This was followed by concentration in a centrifuge with full casing and with a slenderness ratio of about 3, a conical part with an angle of 10°, a dry section of 115 mm caused by difference of 20 mm between the overflow and sediment discharge diameters), a suspension feed approximately at the cylindrical/conical junction and a surface loading of 0.8 $l/(m^2 \cdot h)$. The solid in the resulting sediment fraction contained 46% by weight of riboflavin, and the riboflavin losses were 6.5% of the initial suspension.

EXAMPLE 5

Comparative Example: Only Thermal Treatment Not According To The Invention

A fermentation suspension with approximately the composition described in Example 1 was heat-treated as in Comparative Example 4.

This was followed by concentration in a centrifuge with full casing and with a slenderness ratio of about 3, a conical part with an angle of 10°, overflow diameter = sediment discharge diameter, suspension feed approximately at the cylindrical/conical junction and with a surface loading of 1.1 l/(m²·h). The differential speed of rotation was adjusted to the feed rate so that no solid residue was produced.

The solid in the resulting sediment fraction contained 58% by weight riboflavin, and the riboflavin losses were 4.4%.

We claim:

1. A process for removing riboflavin from fermentation suspensions by centrifugation, which consists essentially of:
   a) heating the fermentation suspension at from 50° to 90° C. for from 1 to 3 hours;
   b) cooling the suspension to from 0° to 30° C. over a period of from 1 to 10 hours, and thereafter,
   c) centrifuging the suspension in a decanting centrifuge operated by the classification principle whereby a sediment fraction is formed which contains at least 60% by weight of solid riboflavin crystals and a liquid fraction is formed which contains essentially no crystalline riboflavin but does contain a large part of the complex cellular constituents of the suspension, whereby undesirable dilution with water of the fermentation suspension is not required.

2. The process of claim 1, wherein the sediment fraction from (c) is resuspended in from 0.5 to 2 parts by volume of water per part by volume of sediment fraction and the new suspension is subjected one or more times to the centrifuging procedure of (c), whereby a sediment fraction is formed containing from 75 to 88% by weight of pure riboflavin.

3. The process of claim 1, wherein the fermentation suspension is heated for from 1 to 2 hours.

4. The process of claim 1, wherein the fermentation suspension is heated for from 1 to 2 hours at a temperature of from 60° to 75° C.

5. The process of claim 1, wherein the fermentation suspension is cooled over a period of from 1 to 5 hours to a temperature of from 0° to 30° C.

6. A process for removing riboflavin from fermentation suspensions defined in claim 1, wherein the centrifugation in step c) is carried out in a decanting centrifuge which has a full casing and a helical conveyor and has a slenderness ratio of 4 or greater and a conical part with an angle of from 10° to 25°, and which is operated by the classification principle with the overflow diameter being equal to the sediment discharge diameter ±10 mm.

7. A process for removing riboflavin from fermentation suspensions as defined in claim 1, wherein the centrifugation in step c) is carried out in a decanting centrifuge with full casing and a helical conveyor and with a slenderness ratio of 4 or greater and a conical part with an angle of from 10° to 25°, and it is operated by the classification principle with the differential speed of rotation of the helical conveyor being from ±0.1 to ±1% of the speed of rotation of the bowl and the surface loading being from 0.8 to 1.8 l/(m²·h) for the first decantation and from 0.2 to 0.8 l/(m²·h) if the decantation is repeated.

8. A process for removing riboflavin from fermentation suspensions as defined in claim 7, wherein the surface loading is from 1 to 1.5 l/(m²·h) in the first decantation and from 0.4 to 0.6 l/(m²·h) if the decantation is repeated.

* * * * *

UNITED STATES PATENT AND TRADEMARK OFFICE
CERTIFICATE OF CORRECTION

PATENT NO. : 5,169,759

DATED : December 8, 1992

INVENTOR(S) : FAUST et al.

It is certified that error appears in the above-identified patent and that said Letters Patent is hereby corrected as shown below:

On title page, item [75] "Walter Gosele" should read --Walter Goesele--

Signed and Sealed this

Twenty-sixth Day of October, 1993

Attest:

BRUCE LEHMAN

Attesting Officer

Commissioner of Patents and Trademarks